United States Patent
Burckhardt et al.

(10) Patent No.: US 9,732,180 B2
(45) Date of Patent: *Aug. 15, 2017

(54) METAL COMPLEX COMPOUNDS AS CATALYSTS FOR POLYURETHANE COMPOSITIONS

(71) Applicant: SIKA TECHNOLOGY AG, Baar (CH)

(72) Inventors: Urs Burckhardt, Zürich (CH); Rita Cannas, Dübendorf (CH)

(73) Assignee: SIKA TECHNOLOGY AG, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/359,772

(22) PCT Filed: Dec. 12, 2012

(86) PCT No.: PCT/EP2012/075204
§ 371 (c)(1),
(2) Date: May 21, 2014

(87) PCT Pub. No.: WO2013/087681
PCT Pub. Date: Jun. 20, 2013

(65) Prior Publication Data
US 2014/0303321 A1 Oct. 9, 2014

(30) Foreign Application Priority Data

Dec. 12, 2011 (EP) ..................... 11193041

(51) Int. Cl.
| | |
|---|---|
| *C08G 18/22* | (2006.01) |
| *C08G 18/26* | (2006.01) |
| *C08G 18/24* | (2006.01) |
| *C08G 65/337* | (2006.01) |
| *C08G 65/328* | (2006.01) |
| *C07F 15/00* | (2006.01) |
| *C07F 7/00* | (2006.01) |

(Continued)

(52) U.S. Cl.
CPC ............ *C08G 18/222* (2013.01); *C07F 1/005* (2013.01); *C07F 1/08* (2013.01); *C07F 1/10* (2013.01); *C07F 1/12* (2013.01); *C07F 3/003* (2013.01); *C07F 3/06* (2013.01); *C07F 5/003* (2013.01); *C07F 5/069* (2013.01); *C07F 7/003* (2013.01); *C07F 7/006* (2013.01); *C07F 7/2232* (2013.01); *C07F 7/24* (2013.01); *C07F 7/28* (2013.01); *C07F 7/30* (2013.01); *C07F 9/005* (2013.01); *C07F 9/902* (2013.01); *C07F 9/908* (2013.01); *C07F 9/94* (2013.01); *C07F 11/005* (2013.01); *C07F 13/005* (2013.01); *C07F 15/00* (2013.01); *C07F 15/0006* (2013.01); *C07F 15/0013* (2013.01); *C07F 15/0026* (2013.01); *C07F 15/0053* (2013.01); *C07F 15/0066* (2013.01); *C07F 15/0093* (2013.01); *C07F 15/02* (2013.01); *C07F 15/025* (2013.01); *C07F 15/045* (2013.01); *C07F 15/065* (2013.01); *C08G 18/227* (2013.01); *C08G 18/24* (2013.01); *C08G 18/26* (2013.01); *C08G 18/3206* (2013.01); *C08G 18/7664* (2013.01); *C08G 65/328* (2013.01); *C08G 65/337* (2013.01); *C09D 175/08* (2013.01)

(58) Field of Classification Search
CPC .... C07F 1/005; C07F 1/08; C07F 1/10; C07F 1/12; C07F 3/003; C07F 3/06; C07F 5/003; C07F 5/069; C07F 7/003; C07F 7/006; C07F 7/2232; C07F 7/24; C07F 7/28; C07F 7/30; C07F 9/005; C07F 9/902; C07F 9/908; C07F 9/94; C07F 11/005; C07F 13/005; C07F 15/00; C07F 15/0006; C07F 15/0013; C07F 15/0026; C07F 15/0053; C07F 15/0066; C07F 15/0093; C07F 15/02
See application file for complete search history.

(56) References Cited

U.S. PATENT DOCUMENTS 2,848,364 A * 8/1958 Habicht et al. ............... 514/629
5,145,997 A * 9/1992 Schwartz et al. ............. 564/158
(Continued)

FOREIGN PATENT DOCUMENTS

| EP | 0000487 | * | 2/1979 |
|---|---|---|---|
| JP | 09-208547 | * | 8/1997 |

(Continued)

OTHER PUBLICATIONS

Grant et al.; Grant & Hackh's Chemical Dictionary, Fifth Edition; Mcgraw-Hill Book Company; New York; 1987; p. 598.*
(Continued)

*Primary Examiner* — Rabon Sergent
(74) *Attorney, Agent, or Firm* — Oliff PLC

(57) ABSTRACT

The invention relates to metal complex compounds of the formula $M_k(L)_x(Y)_{kz-nx}$, where the ligand L has the formula (I), and to metal complex compounds which include the reaction product of at least one salt or a complex of a transition metal or a main group metal element of the groups 13 to 15 and at least one 1,3-ketoamide. Such complex compounds are suitable in particular as catalysts for polyurethane compositions. The invention also relates to two-component polyurethane compositions including at least one polyisocyanate as the first component, at least one polyol as the second component, and at least one such metal complex compound as the catalyst. The invention additionally relates to different uses of the two-component polyurethane compositions.

16 Claims, No Drawings

(51) Int. Cl.

| | |
|---|---|
| *C07F 9/00* | (2006.01) |
| *C07F 1/00* | (2006.01) |
| *C07F 5/00* | (2006.01) |
| *C07F 13/00* | (2006.01) |
| *C07F 11/00* | (2006.01) |
| *C07F 3/00* | (2006.01) |
| *C07F 15/06* | (2006.01) |
| *C07F 15/02* | (2006.01) |
| *C07F 15/04* | (2006.01) |
| *C07F 1/12* | (2006.01) |
| *C07F 1/08* | (2006.01) |
| *C07F 1/10* | (2006.01) |
| *C07F 7/24* | (2006.01) |
| *C07F 5/06* | (2006.01) |
| *C07F 7/22* | (2006.01) |
| *C07F 7/28* | (2006.01) |
| *C07F 9/90* | (2006.01) |
| *C07F 7/30* | (2006.01) |
| *C07F 3/06* | (2006.01) |
| *C07F 9/94* | (2006.01) |
| *C08G 18/32* | (2006.01) |
| *C08G 18/76* | (2006.01) |
| *C09D 175/08* | (2006.01) |

(56) References Cited

U.S. PATENT DOCUMENTS

| | | |
|---|---|---|
| 6,734,268 B2 | 5/2004 | Moren |
| 2006/0020099 A1* | 1/2006 | Stengel et al. ............ 528/44 |
| 2010/0069575 A1 | 3/2010 | Jansen |
| 2013/0109662 A1 | 5/2013 | Bark et al. |

FOREIGN PATENT DOCUMENTS

| | | | |
|---|---|---|---|
| JP | 09-220853 | * | 8/1997 |
| JP | 2010514649 A | | 5/2010 |
| JP | 2013522343 A | | 6/2013 |
| WO | WO 2011/117225 A1 | | 9/2011 |
| WO | 2012/003478 A2 | | 1/2012 |

OTHER PUBLICATIONS

Sax et al.; Hawley's Condensed Chemical Dictionary, Eleventh Edition; Van Nostrand Reinhold; New York; 1987; p. 1170.*
Mar. 27, 2013 International Search Report issued in International Application No. PCT/EP2012/075204.
Nov. 12, 2015 Office Action issued in Chinese Application No. 201280060785.0.
Aug. 30, 2016 Office Action issued in Japanese Application No. 2014-546475.
Dec. 9, 2016 Office Action issued in Chinese Application No. 201280060785.0.

* cited by examiner

METAL COMPLEX COMPOUNDS AS CATALYSTS FOR POLYURETHANE COMPOSITIONS

TECHNICAL FIELD

The present invention concerns the field of polyurethane compositions as well as catalysts for polyurethane compositions.

PRIOR ART

Polyurethane compositions have long been known and are used in various fields. Classically, a distinction is drawn in the technical world between single-component and two-component polyurethane compositions. Single-component polyurethane compositions harden under the influence of the humidity in the air. Two-component polyurethane compositions contain, as a second component, a curing component, which essentially contain polyamines and/or polyols. In both instances, compounds containing isocyanate groups or prepolymers are used.

To hasten the curing, catalysts are added. While a lot of polyurethane catalysts are known, many of them are not especially selective in terms of the urethanization reaction, i.e., the reaction of alcohol OH groups with isocyanate groups, but instead also catalyze more or less other reactions of the isocyanate group, such as formation of allophanate and biuret or cyclotrimerization. In particular, the urethanization reaction usually stands in competition to the reaction of the isocyanate groups with water, which liberates gaseous carbon dioxide to form urea groups. This secondary reaction is troublesome in many polyurethane compositions, especially when used as an adhesive and sealant, as a coating or as a casting resin, since upon curing it results in bubble formation and thus worse shape stability, less adhesion, lower mechanical strength, unsatisfactory aesthetics, and not very reproducible results. The water responsible for the bubble formation either comes from the residual water content of the components of the composition, especially the polyols and the fillers, which even after drying processes are more or less moist and have a typical residual water content of 0.01 to 0.5 wt. %, or from the surrounding humidity, which gets into the composition by diffusion from the air or from the substrates, which is especially common in event of high humidity, porous substrates, and/or hydrophilic polyols, such as the polyether polyols often used in practice. Especially the amine catalysts often used in practice, such as tertiary amines, and tin catalysts such as dialkyl tin carboxylates, often lead to pronounced bubble formation. The residual water content in the polyurethane composition furthermore has the effect that hydrolysis-sensitive catalysts, such as bismuth carboxylates, are deactivated during lengthy keeping (storage) of the composition prior to use, which has a negative effect on the curing rate and the mechanical properties. In the case of some of the known catalysts, such as the dialkyl tin carboxylates, the strength of the cured composition under thermal stress is also inadequate, the catalyst causing a decrease in molecular weight, i.e., a depolymerization, with loss of mechanical strength. Furthermore, many of the known catalysts are solid at room temperature and not very soluble in the starting materials of the polyurethane or the plasticizers, so that organic solvents have to be employed for their use in compositions that harden at room temperature. Finally, many of the known catalysts are toxicologically questionable, especially those based on heavy metal compounds.

The use of monofunctional 1,3-ketoamides without polyether structural units as inhibitors for copper (II) catalyzed unsaturated polyester resins is known from US 2010/0069575. U.S. Pat. No. 6,734,268 describes, among other things, the use of 1,3-ketoamides, also generically including polyether types, as "decomplexers" for metal salt-catalyzed, radically curing adhesives, especially those based on (meth)acrylate. Suitable metal salts mentioned are metal salts that are derived from copper, vanadium, chromium, ruthenium, iron, manganese, nickel, antimony and palladium. These are complexed with ligands, such as amines, alkoxides, etc., and activated with decomplexers to accelerate the hardening. As an example, 1-acetoacetaniline is mentioned as a decomplexer for the complex consisting of Cu(II)-bromide and N,N-dimethylacrylamide.

Presentation of the Invention

The problem of the present invention is to eliminate the above described drawbacks of the prior art. In particular, the problem of the present invention is to provide a catalyst that results in an improvement of the subsequent properties or a balanced ratio of these properties.

The catalyst should be distinguished by a high catalytic activity and selectivity in regard to the urethanization reaction, i.e., the reaction of alcohol OH groups with isocyanate groups, and thus enable a rapid build-up of a mechanically strong polyurethane polymer of polyfunctional alcohols (polyols) and polyisocyanates as little disturbed as possible by moisture. On the other hand, the catalyst should have a sufficient resistance to hydrolysis so that it can remain intact under usual storage conditions, i.e., at room temperature or slightly higher temperature, for several months in a polyol composition containing residual water with no major loss of activity. Furthermore, the catalyst should lower the thermal resistance of the cured polyurethane polymer as little as possible. Moreover, the catalyst should be liquid at room temperature or at slightly elevated temperature and be well soluble in the polyurethane starting materials or in plasticizers, so that it can be easily used in solvent-free systems hardening at room temperature. Finally, the catalyst should have the least possible toxicity.

Now, surprisingly, a new metal complex compound has been found according to claim 1 with the desired properties. The new metal complex compound has the formula $M_k(L)_x(Y)_{kz-nx}$, where M stands for a z-valent metal cation chosen from metal cations and oxometal cations of the transitional metals or the main metal group elements of groups 13 to 15, k stands for a whole number from 1 to 20, x stands for 1, 2, 3 or 4, z stands for 2, 3 or 4, n stands for 1, 2 or 3, Y stands for a single negatively charged ligand and L stands for a ligand of formula (I),

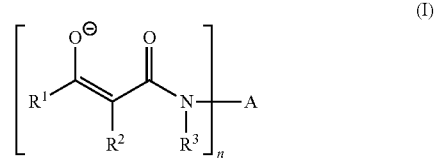

where $R^1$ and $R^2$ independently of each other stand for a hydrogen residue, a monovalent saturated or unsaturated hydrocarbon residue with 1 to 10 carbon atoms, or stand together for a divalent alkylene residue with 3 to 6 carbon atoms, $R^3$ stands for a hydrogen residue, a monovalent saturated hydrocarbon residue that optionally contains heteroatoms, with 1 to 12 carbon atoms, or together for a divalent alkylene residue, which optionally contains heteroatoms, with 3 to 6 carbon atoms, and A stands for a polyoxyalkylene residue or a residue of a polyoxyalkylated compound, optionally with one or two terminal 1,3-ketoamide groups of formula

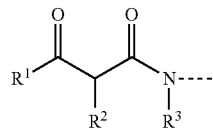

The metal cation is preferably a metal cation or oxometal cation of scandium, yttrium, lanthanum, titanium, zirconium, hafnium, vanadium, niobium, tantalum, chromium, molybdenum, tungsten, manganese, iron, cobalt, nickel, copper, zinc, aluminum, gallium, indium, germanium, tin, lead, antimony and bismuth, especially preferably a metal cation or oxometal cation of lanthanum, titanium, zirconium, molybdenum, iron, zinc, tin and bismuth. Very especially preferred are the dioxomolybdenum (VI), iron (III), zinc (II), bismuth (III) and zirconium (IV) cation, since these have an especially high catalytic activity and selectivity in regard to the urethanization reaction.

In the metal complex compound according to the invention of formula $M_k(L)_x(Y)_{kz-nx}$, A stands for a polyoxyalkylene residue or a residue of a polyoxyalkylated compound, which preferably has a mean molecular weight $M_n$ of around 200 to 5000 g/mol, and especially preferably around 200 to 2000 g/mol. Too low a molecular weight has the drawback that the solubility of the metal complex compound according to the invention has a tendency to be low, while too high a molecular weight leads to the metal content of the metal complex compound according to the invention being low and its catalytic activity per unit of weight thus has a tendency to be slight.

The metal complex compound according to the invention of formula $M_k(L)_x(Y)_{kz-nx}$ constitutes a mononuclear or polynuclear complex compound with one or more metal cations as the central atom and one or more 1,3-ketoamide anions of formula (I) as ligands, being coordination-bound by 1,3-ketoamide groups to the central atom and possibly bridging over two or three central atoms, if n stands for 2 or 3. In this case, the metal complex compound according to the invention can constitute a polynuclear complex compound with k=2 to 20.

Preferably, k stands for a whole number from 1 to 10, especially preferably a whole number from 1 to 5 and very especially preferably it stands for 1. In the latter case, the metal complex compound according to the invention is thus mononuclear. It has a tendency to low viscosity and good solubility.

Preferably, n stands for 1 or 2, since such metal complex compounds have a tendency to have a low viscosity and a good solubility.

Especially preferred are metal complex compounds according to the invention in which k stands for 1 and n for 1 or k stands for 1 and n for 2.

Likewise preferred are metal complex compounds according to the invention of formula $M_k(L)_x(Y)_{kz-nx}$, in which k stands for 1, n stands for 1 or 2 and M is a dioxomolybdenum (VI), an iron (III), a zinc (II), a bismut (III) or a zirconium (IV) cation.

Very especially preferred are metal complex compounds of formula $M_k(L)_x(Y)_{kz-nx}$, in which M is an iron (III) cation, k is 1, x is 3 and kz-nx is 0, or M is a dioxomolybdenum (VI) cation, k is 1, x is 2 and kz-nx is 0, or M is a zinc (II) cation, k is 1, x is 2 and kz-nx is 0, or M is a bismuth (III) cation, k is 1, x is 3 and kz-nx is 0, or M is a zirconium (IV) cation, k is 1, x is 4 and kz-nx is 0.

The ligand L of formula (I) formally has a single negative charge delocalized over the 1,3-ketoamide structure. It can therefore be drawn in various boundary structures, such as the following depicted boundary structures. All possible boundary structures of the ligand L of formula (I) are considered to be equivalent in the context of the present invention.

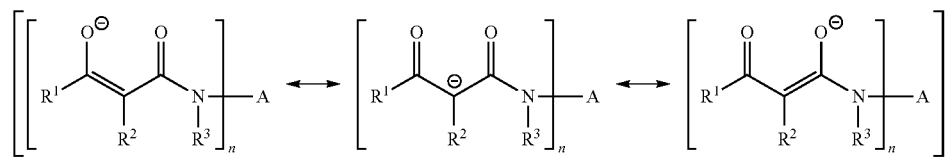

The ligand Y constitutes any given single negatively charged ligand, especially a suitable organic anion, preferably a carbonylate, especially preferably a 1,3-dicarbonylate, such as acetylacetonate or 2,2,6,6-tetramethylheptane-3,5-dionate.

The metal complex compound according to the invention of formula $M_k(L)_x(Y)_{kz-nx}$ with M as the central atom and coordination-bound ligand L of formula (I) and optionally Y is neutral.

The ligands L of formula (I) can be the same or different. Especially preferably, the same ligands L of formula (I) are present.

In formula (I), $R^1$ and $R^2$ independently of each other stand for a hydrogen residue, a monovalent saturated or unsaturated hydrocarbon residue with 1 to 10 carbon atoms, or together a divalent alkylene residue with 3 to 6 carbon atoms.

The monovalent saturated hydrocarbon residue with 1 to 10 carbon atoms is preferably an alkyl residue with 1 to 4 carbon atoms, especially a methyl, propyl, isopropyl or a butyl residue. These have the benefit that the metal complex compound thus has a tendency to be liquid or easily soluble. Very especially preferably, the alkyl residue with 1 to 4 carbon atoms is a methyl residue. The monovalent unsaturated hydrocarbon residue is preferably an aryl residue, especially a phenyl residue.

Preferably $R^1$ and $R^2$ together form a divalent methyl residue with 3 to 4 carbon atoms, especially with 3 carbon atoms.

Especially preferably, $R^2$ is a hydrogen residue, since the metal complex compound thus has a tendency to be especially stable.

By a divalent alkylene residue with 3 to 6 carbon atoms is meant a residue of formula $-(CH_2)_n-$, where n signifies 3 to 6.

R³ stands for a hydrogen, a monovalent saturated hydrocarbon residue, which optionally contains heteroatoms, with 1 to 12 carbon atoms, a benzyl residue, or together a divalent alkylene residue, optionally containing heteroatoms, with 3 to 6 carbon atoms.

The monovalent saturated hydrocarbon residue with 1 to 12 carbon atoms is preferably an alkyl residue with 1 to 8 carbon atoms, especially preferably a methyl, an ethyl, a propyl, an isopropyl, a butyl, an isobutyl, a 2-butyl or a 2-ethyl-hexyl residue. This has the benefit that the metal complex compound thus has a tendency to be liquid or easily soluble.

Especially preferably, R³ stands for a hydrogen, methyl or isopropyl residue.

The choice of the preferred residues in the ligand L of formula (I) is preferably based on the fact that the corresponding 1,3-ketoamides which are used as the starting materials for the preparation of the metal complex compound according to the invention of formula $M_k(L)_x(Y)_{kz-nx}$ are easy to produce and/or commercially available and thus economical in price.

The invention also concerns a method for production of metal complex compounds, wherein a 1,3-ketoamide of formula

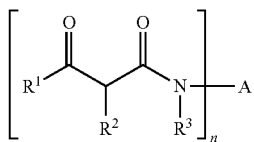

with R¹, R², R³, A and n as defined above, is reacted with a metal salt or metal complex, chosen from a salt or a complex of a transitional metal or an element of the main metal groups 13 to 15.

Preferred are salts or complexes of scandium, yttrium, lanthanum, titanium, zirconium, hafnium, vanadium, niobium, tantalum, chromium, molybdenum, tungsten, manganese, iron, cobalt, nickel, copper, zinc, aluminum, gallium, indium, germanium, tin, lead, antimony and bismuth. Especially preferred are salts or complexes of lanthanum, titanium, zirconium, molybdenum, iron, zinc, tin and bismuth. Very especially preferred are dioxomolybdenum (VI), iron (III), zinc (II), bismuth (III) and zirconium (IV) salts or complexes.

Preferred salts of these metals are dichlorides and carbonates. Preferred complexes of these metals are dicarboxylates and 1,3-diketonates. The latter complexes are very especially preferred.

The stoichiometry between the salt and the complex of the transitional metal or the element of the main metal groups 13 to 15 and the 1,3-ketoamide is preferably adjusted so that the number of the 1,3-ketoamide groups corresponds at least to the valency z of the metal atom. For example, for 1 mol of bismuth (III) carboxylate there is used preferably at least 3 mol of 1,3-ketoamide with n=1 or 1.5 mol of 1,3-ketoamide with n=2.

The 1,3-ketoamide used is preferably obtained by reacting a polyether amine with diketene or a 1,3-ketoester.

Preferred polyetheramines are polyoxyalkylene amines, preferably with a mean molecular weight $M_n$ of around 200 to 5000 g/mol, such as are commercially available under the brand names Jeffamine® (from Huntsman), Polyetheramine (from BASF) or PC Amine® (from Nitroil), Especially preferred types are Jeffamine® M-600, Jeffamine® M-1000, Jeffamine® M-2000, Jeffamine® M-2070, Jeffamine® XTJ-249, Jeffamine® XTJ-435, Jeffamine® XTJ-436, Jeffamine® XTJ-581, Jeffamine® D-230, Jeffamine® D-400, Jeffamine® D-2000, Jeffamine® D-4000, Jeffamine® XTJ-582, Jeffamine® XTJ-578, Jeffamine® HK-511, Jeffamine® ED-600, Jeffamine® ED-900, Jeffamine® ED-2003, Jeffamine® XTJ-568, Jeffamine® XTJ-569, Jeffamine® XTJ-533, Jeffamine® XTJ-536, Jeffamine® XTJ-542, Jeffamine® XTJ-548, Jeffamine® XTJ-559, Jeffamine® SD-231, Jeffamine® SD-401, Jeffamine® SD-2001, Jeffamine® T-403, Jeffamine® T-3000, Jeffamine® T-5000, Jeffamine® XTJ-566 and Jeffamine® ST-404 (all from Huntsman), as well as the analogous types from BASF and Nitroil. Especially preferred are polyoxyalkylene amines with a mean molecular weight $M_n$ of around 200 to 2000 g/mol. Very especially preferred are polyoxypropylene amines, especially polyoxypropylene monoamines and polyoxypropylene diamines, which optionally contain moieties of other oxyalkylene units such as oxybutylene and especially oxyethylene units. Suitable as the polyoxypropylene monoamines are especially the types Jeffamine® M-600, Jeffamine® M-1000 and Jeffamine® XTJ-581. Suitable as polyoxypropylene diamines are especially the types Jeffamine® D-230, Jeffamine® D-400, Jeffamine® D-2000, Jeffamine® XTJ-582, Jeffamine® XTJ-578, Jeffamine® SD-231, Jeffamine® SD-401 and Jeffamine® SD-2001.

Preferred 1,3-ketoesters are alkylacetoacetates, especially preferably methylacetoacetate, ethylacetoacetate and tert. butylacetoacetate.

Preferably the production of the 1,3-ketoamide occurs by heating the mixture of the polyetheramine and the diketene or the 1,3-ketoester preferably under stirring at 100 to 500 mbar, especially preferably around 300 mbar, preferably for 1 to 20 hours, especially preferably around 4 hours, at a temperature of preferably 50 to 150° C., especially preferably around 110° C. After this, the reaction mixture is liberated of volatile compounds preferably in a vacuum.

The 1,3-ketoamide can also preferably be obtained by adding the diketene or the 1,3-ketoester preferably slowly to a polyetheramine heated to preferably 80 to 160° C., especially preferably around 130° C., and holding the reaction mixture preferably for another 10 to 30 hours, especially preferably around 18 hours, at 80 to 160° C., preferably around 130° C. After this, cooling is done preferably to room temperature and the mixture is liberated of volatile components, preferably in a vacuum. The obtained residue is preferably dissolved in ethyl acetate, the solution is washed with hydrochloric acid, dried with magnesium sulfate, and concentrated down completely.

As mentioned above, the use of dioxomolybdenum (VI), iron (III), zinc (II) and bismuth (III) salts or complexes is preferred.

The preparation of the preferred dioxomolybdenum (VI) complex compound is done preferably by mixing the dioxomolybdenum (VI) salt or complex with the 1,3-ketoamide and heating the mixture preferably under stirring for 1 to 24 hours, preferably around 2 hours, to a temperature of 50 to 130° C., preferably around 80° C. After this, the reaction mixture is liberated of volatile components, preferably in a vacuum.

The preparation of the likewise preferred iron (III) complex compound is done preferably by mixing the iron (III) salt or complex with the 1,3-ketoamide and heating the mixture preferably under stirring for 1 to 24 hours, preferably around 5 hours, to a temperature of 50 to 130° C., preferably around 90° C. After this, the reaction mixture is liberated of volatile components, preferably in a vacuum.

The preparation of the likewise preferred zinc (II) complex compound is done preferably by mixing the zinc (II) salt or complex with the 1,3-ketoamide and heating the mixture preferably under stirring for 1 to 24 hours, preferably around 3 hours, to a temperature of 50 to 130° C., preferably around 90° C. After this, the reaction mixture is liberated of volatile components, preferably in a vacuum.

The likewise preferred bismuth (III) complex compounds can preferably be obtained by mixing the bismuth (III) salt or complex with the 1,3-ketoamide and heating the mixture preferably under stirring for 1 to 24 hours, preferably around 2 hours, to a temperature of 50 to 130° C., preferably around 80° C. After this, the reaction mixture is preferably cooled down, preferably to room temperature.

The invention also concerns the metal complex compounds obtainable with the above described methods, i.e., metal complex compounds which comprise the reaction products of at least one salt or one complex of a transitional metal or an element of the main metal groups 13 to 15 and at least one 1,3-ketoamide of formula

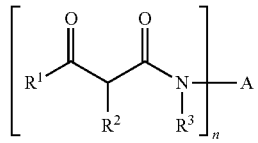

where $R^1$, $R^2$, $R^3$, A and n have the above given definitions.

The metal complex compounds according to the invention can be used as catalyst for curable masses, preferably for polyurethane compositions. The metal complex compound according to the invention accelerates the curing of curable masses which have reactive groups capable of entering into cross-linking reactions. In particular, the metal complex compound according to the invention accelerates the curing of two-component polyurethane compositions which cross-link with themselves and optionally under the influence of moisture across blocked or especially free isocyanate groups. Especially accelerated is the urethanization reaction, i.e., the reaction of isocyanate groups with alcohol OH groups. The compositions being cross-linked can also contain other reactive groups capable of entering into cross-linking reactions, especially, alkoxysilane groups. Preferably, these are trialkoxysilane groups, such as are contained in silane bonding agents.

The metal complex compounds according to the invention can be used advantageously as a catalyst in a two-component polyurethane composition. This comprises, besides the metal complex compound according to the invention, a polyol as the first component and a polyisocyanate as the second component.

By "two-component" is meant a composition in which its ingredients are present in two different components, which are kept in separate containers, and each of which has storage stability. Shortly before or during the application of the composition, the two components are mixed together, whereupon the mixed composition hardens, the hardening on occasion occurring or being completed only by the action of moisture and/or elevated temperature.

Substances names starting with "poly", such as polyol or polyisocyanate, designate substances that formally contain two or more of the functional groups appearing in their name in each molecule.

The term "polyisocyanate" comprises compounds with two or more isocyanate groups, regardless of whether they are monomeric diisocyanates, oligomeric polyisocyanates or polymers having isocyanate groups.

Especially suitable as the polyisocyanate is, for example, a polyisocyanate in the form of a monomeric di- or triisocyanate or an oligomer of a monomeric diisocyanate or a derivate of a monomeric diisocyanate. Suitable as monomeric di- or triisocyanates are, for example, 1,4-tetramethylene diisocyanate, 2-methylpentamethylene-1,5-diisocyanate, 1,6-hexamethylene diisocyanate (HDI), 2,2,4- and 2,4,4-trimethyl-1,6-hexamethylene diisocyanate (TMDI), 1,10-decamethylene diisocyanate, 1,12-dodecamethylene diisocyanate, lysine- and lysine ester diisocyanate, cyclohexane-1,3 and -1,4-diisocyanate, 1-methyl-2,4- and -2,6-diisocyanatocyclohexane and any given mixtures of these isomers, 1-isocyanato-3,3,5-trimethyl-5-isocyanatomethyl-cyclohexane (=isophorone diisocyanate or IPDI), perhydro-2,4'- and -4,4'-diphenylmethane diisocyanate (HMDI), 1,4-diisocyanato-2,2,6-trimethylcyclohexane (TMCDI), 1,3- and 1,4-bis-(isocyanatomethyl)-cyclohexane, m- and p-xylylene diisocyanate (m- and p-XDI), m- and p-tetramethyl-1,3- and -1,4-xylylene diisocyanate (m- and p-TMXDI), bis-(1-isocyanato-1-methylethyl)-naphthaline, dimer and trimer fatty acid isocyanates, such as 3,6-bis-(9-isocyanatononyl)-4,5-di-(1-heptenyl)-cyclohexene dimeryl diisocyanate), a,a,a',a',a'',a''-hexamethyl-1,3,5-mesitylene triisocyanate, 2,4- and 2,6-toluylene diisocyanate and any given mixtures of these isomers (TDI), 4,4'-, 2,4'- and 2,2'-diphenylmethane diisocyanate and any given mixtures of these isomers (MDI), mixtures of MDI and MDI-homologues (polymeric MDI or PMDI), 1,3- and 1,4-phenylene diisocyanate, 2,3,5,6-tetramethyl-1,4-diisocyanatobenzene, naphthaline-1,5-diisocyanate (NDI), 3,3'-dimethyl-4,4'-diisocyanatodiphenyl (TODI), dianisidine diisocyanate (DADI), 1,3,5-tris-(isocyanatomethyl)-benzene, tris-(4-isocyanatophenyl)-methane and tris-(4-isocyanatophenyl)-thiophosphate.

Preferred polyisocyanates are the usual commercial diisocyanates. Especially preferred are HDI, IPDI, TDI and MDI as well as oligomers of diisocyanates and polyurethane polymers having isocyanate groups (NCO-prepolymers).

As the polyols, one can use, for example, the following commercially available polyols or mixtures thereof:

polyoxyalkylene polyols, also known as polyether polyols or oligoetherols, which are polymerization products of ethylene oxide, 1,2-propylene oxide, 1,2- or 2,3-butylene oxide, oxetane, tetrahydrofuran or mixtures thereof, possibly polymerized with the aid of a starter molecule with two or more active hydrogen atoms such as water, ammonia or compounds with several OH or NH groups, such as 1,2-ethane diol, 1,2- and 1,3-propane diol, neopentyl glycol, diethylene glycol, triethylene glycol, the isomeric dipropylene glycols and tripropylene glycols, the isomeric butane diols, pentane diols, hexane diols, heptane diols, octane diols, nonane diols, decane diols, undecane diols, 1,3- and 1,4-cyclohexane dimethanol, bisphenol A, hydrogenated bisphenol A, 1,1,1-trimethylol ethane, 1,1,1-trimethylol propane, glycerine, aniline, as well as mixtures of the aforementioned compounds. One can use both polyoxyalkylene polyols that have a low degree of unsaturation (measured according to ASTM D-2849-69 and indicated as milliequivalent unsaturation per gram of polyol (mEq/g)), prepared for example with the aid of so-called Double Metal Cyanide Complex Catalysts (DMC Catalysts), and polyoxyalkylene polyols with a higher degree of unsaturation, prepared for example with the aid of anionic catalysts such as NaOH, KOH, CsOH or alkaline alcoholates.

Especially suitable are polyoxyalkylene diols or polyoxyalkylene triols, especially polyoxyethylene and polyoxypropylen di- and triols. Especially suitable are polyoxyalkylene diols and triols with a degree of unsaturation lower than 0.02 mEq/g and with a molecular weight in the range of 1000-30,000 g/mol, as well as polyoxypropylene diols and triols with a molecular weight of 400-8000 g/mol.

Likewise especially suitable are so-called ethylene oxide-terminated ("EO-endcapped", ethylene oxide-endcapped) polyoxypropylene polyols. The latter are special polyoxypropylene polyoxyethylene polyols, which are obtained for example in that pure polyoxypropylene polyols, especially polyoxypropylene diols and triols, after the completion of the polypropoxylation reaction, are further alkoxylated with ethylene oxide and therefore have primary hydroxyl groups.

styrene-acrylonitrile or acrylonitrile-methylmethacrylate grafted polyether polyols.

polyester polyols, also known as oligoesterols, prepared by known methods, especially the polycondensation of hydroxycarboxylic acids or the polycondensation of aliphatic and/or aromatic polycarboxylic acids with divalent or polyvalent alcohols.

Especially suitable as polyester polyols are those which are prepared from divalent to trivalent, especially divalent alcohols, such as ethylene glycol, diethylene glycol, propylene glycol, dipropylene glycol, neopentyl glycol, 1,4-butane diol, 1,5-pentane diol, 3-methyl-1,5-hexane diol, 1,6-hexane diol, 1,8-octane diol, 1,10-decane diol, 1,12-dodecane diol, 1,12-hydroxystearyl alcohol, 1,4-cyclohexane dimethanol, dimer fatty acid diol (dimer diol), hydroxypivalinic acid neopentyl glycol ester, glycerine, 1,1,1-trimethylol propane or mixtures of the aforementioned alcohols, with organic di- or tricarboxylic acids, especially dicarboxylic acids, or their anhydrides or esters, such as succinic acid, glutaric acid, adipic acid, trimethyladipic acid, suberic acid, azelaic acid, sebacic acid, dodecane dicarboxylic acid, maleic acid, fumaric acid, dimere fatty acid, phthalic acid, phthalic acid anhydride, isophthalic acid, terephthalic acid, dimethyl terephthalate, hexahydrophthalic acid, trimellithic acid and trimellithic acid anhydride, or mixtures of the aforementioned acids, as well as polyester polyols of lactones, such as ε-caprolactone and starters like the aforementioned divalent or trivalent alcohols.

polycarbonate polyols, such as can be obtained by reacting, for example, the aforementioned alcohols—used to construct the polyester polyols—with dialkyl carbonates, diaryl carbonates or phosgene.

block copolymers having at least two hydroxyl groups, which have at least two different blocks with polyether, polyester, and/or polycarbonate structure of the above-described kind, especially polyether polyester polyols.

polyacrylate and polymethacrylate polyols.

polyhydroxyfunctional fats and oils, such as natural fats and oils, especially ricinus oil; or polyols obtained by chemical modification of natural fats and oils—so-called oleochemical polyols, such as the epoxypolyesters or epoxypolyethers obtained by epoxidation of unsaturated oils and subsequent ring opening with carboxylic acids or alcohols, or polyols obtained by hydroformylation and hydrogenation of unsaturated oils; or polyols obtained from natural fats and oils by decomposition processes, such as alcoholysis or ozonolysis and subsequent chemical linking, for example, by transesterification or dimerization, of the so obtained decomposition products or derivatives thereof. Suitable decomposition products of natural fats and oils are in particular fatty acids and fatty alcohols, as well as fatty acid esters, especially the methyl ester (FAME), which can be derivatized for example by hydroformylation and hydrogenation to form hydroxyfatty acid esters.

polycarboxylic polyols, also known as oligohydrocarbonols, such as polyhydroxyfunctional polyolefins, polyisobutylenes, polyisoprenes; polyhydroxyfunctional ethylene-propylene, ethylene-butylene or ethylene-propylenediene copolymers; polyhydroxyfunctional polymers of dienes, especially of 1,3-butadiene, which can also be prepared in particular from anionic polymerization; polyhydroxyfunctional copolymers of dienes such as 1,3-butadiene or diene mixtures and vinyl monomers such as styrene, acrylonitrile, vinyl chloride, vinyl acetate, vinyl alcohol, isobutylene and isoprene, such as polyhydroxyfunctional acrylonitrile/butadiene copolymers, such as can be prepared from epoxides or amino alcohols and carboxyl-terminated acrylonitrile/butadiene copolymers; as well as hydrogenated polyhydroxyfunctional polymers or copolymers of dienes.

The mentioned polyols preferably have a mean molecular weight of 250-30,000 g/mol, especially 400-20,000 g/mol, and furthermore preferably have a mean OH functionality in the range of 1.6 to 3.

By "molecular weight" is meant always in the case of oligomers or polymers the molecular weight mean $M_n$.

Especially preferred is the use of polyether polyols, preferably polypropylene polyols and polyethylene-polypropylene mixed polyols, as well as polyester polyols and polycarbonate polyols.

The metal complex compound according to the invention is preferably present in the first component, which has the advantage that the polyisocyanate in the second component, which is sensitive to catalytically active compounds, is not impaired in its storage stability (shelf life).

The metal complex compound according to the invention can be used as a single catalyst or also together with other catalysts, such as bismuth, tin, or zirconium compounds or tertiary amines.

The two-component polyurethane composition according to the invention can optionally contain other conventionally used adjuvants and additives, such as pigments, plasticizers or diluents, hardeners, cross-linking agents, chain lengtheners, other catalysts, bonding agents, stabilizers, rheology adjusting agents and drying agents, etc.

The metal complex compound according to the invention, in terms of quantity of elemental metal, is present in the two-component polyurethane composition according to the invention preferably in a quantity of 0.0002 to 1 wt. %, especially preferably in a quantity of 0.001 to 0.5 wt. %, and very especially preferably in a quantity of 0.002 to 0.3 wt. %, in terms of the weight of the composition. Too high quantities have the effect of the open time or processing time of the composition being too short, while the use of too small a quantity has the drawback that the composition is too weakly catalyzed and thus cures too slow, incompletely, and/or defectively. In the two-component polyurethane composition according to the invention the metal complex compound according to the invention amounts to 0.001 to 10, preferably 0.005 to 5, and especially preferably 0.01 to 3 mmol-equivalent metal atoms per 100 g of composition.

If the metal complex compound according to the invention is a dioxomolybdenum (VI) complex compound, then this in terms of quantity of elemental molybdenum is present in the two-component polyurethane composition according to the invention preferably in a quantity of 0.01 to 0.5 wt. %, especially preferably in a quantity of 0.02 to 0.3 wt. %. In the two-component polyurethane composition according to the invention the dioxomolybdenum (VI) complex compound preferably amounts to 0.1 to 5, especially preferably 0.2 to 3 mmol-equivalent molybdenum atoms per 100 g of composition.

If the metal complex compound according to the invention is an iron (III) or zinc (II) complex compound, then in terms of quantity of elemental iron or zinc it is present in the two-component polyurethane composition according to the invention preferably in a quantity of 0.005 to 0.5 wt. %, especially preferably in a quantity of 0.01 to 0.2 wt. %. In the two-component polyurethane composition according to the invention the iron (III) or zinc (II) complex compound according to the invention preferably amounts to 0.05 to 5, especially preferably 0.1 to 2 mmol-equivalent iron or zinc atoms per 100 g of composition.

If the metal complex compound according to the invention is a bismuth (III) complex compound, then in terms of quantity of elemental bismuth it is present in the two-component polyurethane composition according to the invention preferably in a quantity of 0.001 to 0.2 wt. %, especially preferably in a quantity of 0.002 to 0.1 wt. %. In the two-component polyurethane composition according to the invention the bismuth (III) complex compound according to the invention preferably amounts to 0.005 to 1, especially preferably 0.01 to 0.5 mmol-equivalent bismuth atoms per 100 g of composition.

As already mentioned above, the metal complex compound according to the invention, despite its size and polynuclear structure, is relatively active and also relative selective in regard to the urethanization reaction. Thus, the die metal complex compound according to the invention is distinguished from metal compounds without the 1,3-ketoamide by a distinctly higher catalytic activity. The hardening of the two-component polyurethane composition according to the invention generally occurs quickly. The selectivity of the metal complex compound according to the invention, however, does not suffer as a result of the elevated activity: the hardening occurs without bubble formation, even under unfavorable conditions, such as high temperature, high humidity, or high residual water content of the composition or when using polyols with secondary OH groups or hydrophilic polyols. The metal complex compound according to the invention is relatively thermally and hydrolytically stable, it decomposes only slowly, even in a polyol containing residual water, and thus retains its catalytic activity even during lengthy storage time. Even so, the use of the metal complex compound according to the invention leads to good stability of the hardened polyurethane composition under thermal stress. The metal complex compound according to the invention moreover is liquid at room temperature and/or readily soluble in plasticizers or polyols, and thus it can be employed easily and without the use of volatile organic solvents (VOC) in systems hardening at room temperature. Finally, some of the compounds listed among the metal complex compound according to the invention of formula $M_k(L)_x(Y)_{kz-nx}$ are only slightly colored and will hardly cause discolorations of the hardened polyurethane composition, especially when the metal cation or oxometal cation is a zinc (II), a bismuth (III) or a zirconium (IV) cation. Some of the compounds also have a relatively low toxicity, especially those in which the metal cation or oxometal cation is a dioxomolybdenum (VI), an iron (III), a zinc (II), a bismuth (III) or a zirconium (IV) cation.

The two-component polyurethane composition according to the invention can be used in many areas, such as a casting compound, sealant, adhesive, covering, coating, lacquer, primer, hard foam, soft foam, molded piece, elastomer, fiber, film or membrane for construction and industrial applications, for example, as an electrical casting compound, putty, seam sealant, cavity sealant, joint sealant, mounting adhesive, bodywork adhesive, sandwich element adhesive, laminate adhesive, liner adhesive, packaging adhesive, wood adhesive, flooring adhesive, anchoring adhesive, floor covering and coating, balcony and roof coating, concrete protection coating, garage surface coating, pipe coating, corrosion protection coating, textile coating, decorative lacquer, wood lacquer, primer, furniture foam, upholstery foam, filter foam, insulation foam, soundproofing foam, sealing foam, packaging foam, bodywork foam, modeling board, dampening element, sealing element, tires, rollers, bearings, conveyor belt, rubberized thread, shoe soles, housing, window molding, implants, foam rubber, etc.

Preferred areas of application are casting compounds, sealants, adhesives, linings, coatings, lacquers, primers, molded pieces, elastomers for construction and industrial application.

Besides being used in two-component polyurethane compositions, the metal complex compound according to the invention can be used as a catalyst or cocatalyst in other curable masses, such as in single-component polyurethane compositions, in epoxy resins, acrylates and silicones.

EXAMPLES

Description of the Measurement Methods

Infrared spectra were measured on a FT-IR 1600 instrument from Perkin-Elmer (horizontal ATR measuring unit with ZnSe crystal; measurement window 4000-650 $cm^{-1}$). Liquid samples were deposited undiluted as films, solid samples were dissolved in $CH_2Cl_2$. The absorption bands are indicated in wave numbers ($cm^{-1}$).

$^1$H-NMR spectra were measured on a spectrometer of type Bruker DPX-300 at 300.13 MHz; the chemical shifts δ are indicated in ppm relative to tetramethylsilane (TMS). No distinction was made between true and pseudo coupling patterns.

The viscosity was measured on a thermostatically controlled cone-plate viscosimeter Physica MCR 300 (cone diameter 20 mm, cone angle 1°, distance between cone tip and plate 0.05 mm, shear rate 0.1 to 100 $s^{-1}$).

Mass spectra (FIMS) were measured on a high-resolution mass spectrometer of type Thermo Scientific LTQ Orbitrap XL, by injecting 500 μl of the sample dissolved in methanol (100 μg/ml) at an injection rate of 10 μl/min and a flow rate of the carrier (1 mM ammonium formate in methanol) of 500 μl/min directly into the mass spectrometer; the detection was done by means of Electrospray Ionization ($ESI^+$).

Preparation of 1,3-ketoamides

General Preparation Procedure A

In a round-bottom flask, a mixture of a polyether amine and tert.-butyl-acetoacetate was heated under stirring at 300 mbar for around 4 hours to 110° C. After this, the reaction mixture was liberated of the volatile components in vacuum.

General Preparation Procedure B

In a round-bottom flask, tert.-butyl-acetoacetate was added slowly to a polyether amine heated to 130° C. and the reaction mixture was held for another 18 hours at 130° C. After this, it was cooled down to room temperature and liberated of the volatile components in vacuum. The obtained residue was dissolved in ethyl acetate, the solution washed with hydrochloric acid solution (0.1 M), dried with MgSO$_4$ and concentrated down completely.

1,3-Ketoamide 1

According to general preparation procedure A, 12.00 g of Jeffamine® ST-404 and 12.27 g of tert.-butyl-acetoacetate were combined. One obtained 17.39 g of a reddish oil.

FT-IR: 2968, 2931, 2871, 1719, 1362, 1584, 1443, 1371, 1324, 1229, 1216, 1102, 929, 850, 775.

1,3-Ketoamide 2

According to general preparation procedure A, 41.92 g of Jeffamine® SD-2001 and 7.80 g of tert.-butyl-acetoacetate were reacted. One obtained 45.37 g of a light yellow oil.

FT-IR: 2939, 2868, 1737, 1589, 1202, 1449, 1371, 1269, 1217, 1092, 934, 906, 868, 800, 772.

FIMS: m/2149.52 (15), 2148.51733 (10, [MNa$^+$] for the oligomer with x=31), 2144.56 (100), 2143.56.055 (80, [MH$^+$] for the oligomer with x=31).

1,3-Ketoamide 3

According to general preparation procedure A, 103.10 g of Jeffamine® SD-401 and 65.13 g of tert.-butyl-acetoacetate were reacted. One obtained 133.90 g of a light yellow oil.

FT-IR: 2969, 2929, 2870, 1718, 1633, 1584, 1444, 1372, 1341, 1208, 1099, 1018, 928, 862, 773.

1,3-Ketoamide 4

According to general preparation procedure B, 76.50 g of Jeffamine® D-230 and 130.02 g of tert.-butyl-acetoacetate were reacted. One obtained 51.93 g of a light yellow oil.

FT-IR: 3305, 2973, 2875, 1714, 1645, 1542, 1452, 1410, 1358, 1323, 1254, 1147, 1103, 1024, 922, 847, 668.

FIMS: m/z 497.28 (90), 475.30 (54), 439.24 (43), 417.26047 (100, [MH$^+$] for the oligomer with x=3), 359.22 (41).

1,3-Ketoamide 5

According to general preparation procedure B, 15.76 g of Jeffamine® D-400 and 14.99 g of tert.-butyl-acetoacetate were reacted. One obtained 13.21 g of a light yellow oil.

FT-IR: 3306, 2971, 2929, 2869, 1715, 1646, 1540, 1453, 1409, 1369, 1252, 1143, 1098, 1015, 924, 848, 775, 750.

FIMS: m/z 649.42 (30), 623.45 (63), 607.41339 (100, [MNH$_4^+$] for the oligomer with x=6), 591.38 (36).

1,3-Ketoamide 6

According to general preparation procedure B, 82.10 g of Jeffamine® D-2000 and 17.14 g of tert.-butyl-acetoacetate were reacted. One obtained 87.77 g of a light yellow oil.

FT-IR: 3322, 2969, 2867, 1715, 1649, 1535, 1451, 1371, 1343, 1296, 1253, 1095, 1013, 921, 866.

1,3-Ketoamide 7

According to general preparation procedure B, 62.33 g of Jeffamine® M-600 and 22.39 g of tert.-butyl-acetoacetate were reacted. One obtained 58.14 g of a light yellow oil.

FT-IR: 3323, 2969, 2867, 1720, 1649, 1547, 1452, 1371, 1342, 1297, 1095, 1013, 924, 817.

FIMS: m/z 655.47 (95), 641.46 (65), 597.43359 (100, [MNH$_4^+$] for the oligomer with x=8), 583.42 (54), 539.39 (100).

1,3-Ketoamide 8

According to general preparation procedure B, 56.15 g of Jeffamine® XTJ-581 and 15.82 g of tert.-butyl-acetoacetate were reacted. One obtained 32.14 g of a brownish oil.

FT-IR: 3324, 2978, 2864, 1715, 1668, 1540, 1456, 1348, 1275, 1256, 1094, 946, 849, 760.

1,3-Ketoamide 9

According to general preparation procedure A, 12.72 g of Jeffamine® SD-231 and 17.94 g of tert.-butyl-acetoacetate were reacted. One obtained 20.62 g of a reddish-orange oil.

FT-IR: 2974, 2931, 2872, 1715, 1633, 1444, 2362, 1106, 1025, 934, 848, 774.

Preparation of Polyurethane Catalysts

General Preparation Procedure C

In a round-bottom flask, dioxomolybdenum (VI) bis(acetylacetonate) and a 1,3-ketoamide prepared as described were mixed and the mixture was heated under stirring for 2 hours to 80° C. After this, the reaction mixture was liberated of volatile components in vacuum.

Example 1

Catalyst Mo1

According to general preparation procedure C, 3.24 g of dioxomolybdenum (VI) bis(acetylacetonate) and 5.67 g of 1,3-ketoamide 1 were reacted. One obtained 7.86 g of a reddish, glasslike solid.

FT-IR: 2969, 2930, 2873, 1717, 1588, 1496, 1371, 1333, 1266, 1195, 1104, 1028, 991, 931, 903, 776, 734.

Example 2

Catalyst Mo2

According to general preparation procedure C, 3.70 g of dioxomolybdenum (VI) bis(acetylacetonate) and 5.60 g of 1,3-ketoamide 4 were reacted. One obtained 7.42 g of a brownish, glasslike solid.

FT-IR: 3305, 2972, 2930, 2873, 1715, 1588, 1514, 1446, 1401, 1361, 1267, 1182, 1104, 1028, 969, 932, 898, 795, 733, 701, 668.

Example 3

Catalyst Mo3

According to general preparation procedure C, 1.80 g of dioxomolybdenum (VI) bis(acetylacetonate) and 3.66 g of 1,3-ketoamide 5 were reacted. One obtained 4.46 g of a brownish oil.

FT-IR: 2968, 2869, 1720, 1626, 1564, 1517, 1446, 1401, 1369, 1266, 1182, 1092, 1007, 968, 931, 896, 794, 668.

Example 4

Catalyst Mo4

According to general preparation procedure C, 1.52 g of dioxomolybdenum (VI) bis(acetylacetonate) and 11.00 g of 1,3-ketoamide 6 were reacted. One obtained 11.35 g of a greenish, glasslike solid.

FT-IR: 3307, 2969, 2868, 1737, 1629, 1566, 1522, 1451, 1371, 1091, 1011, 934, 906.

Example 5

Catalyst Mo5

According to general preparation procedure C, 2.83 g of dioxomolybdenum (VI) bis(acetylacetonate) and 13.32 g of 1,3-ketoamide 7 were reacted. One obtained 14.42 g of a brownish oil.

FT-IR: 3296, 2969, 2870, 1630, 1566, 1521, 1450, 1403, 1372, 1342, 1268, 1093, 1009, 967, 933, 904, 796.

General Preparation Procedure D

In a round-bottom flask, dried iron (III) tris(acetylacetonate) and a 1,3-ketoamide prepared as described were mixed and the mixture was heated under stirring for 3 hours to 90° C. After this, the reaction mixture was liberated of volatile components in vacuum.

Example 6

Catalyst Fe1

According to general preparation procedure D, 2.65 g of iron (III) tris(acetylacetonate) and 16.54 g of 1,3-ketoamide 7 were reacted. One obtained 17.40 g of a reddish-brown oil.

FT-IR: 3324, 2970, 2868, 1651, 1577, 1523, 1450, 1372, 1342, 1272, 2097, 1016, 968, 926, 864, 775, 667.

Example 7

Catalyst Fe2

According to general preparation procedure D, 1.41 g of iron (III) tris(acetylacetonate) and 15.70 g of 1,3-ketoamide 2 were reacted. One obtained 16.17 g of a brownish-red oil.

FT-IR: 2967, 2865, 1638, 1558, 1512, 1456, 1372, 1335, 1296, 1095, 1013, 926, 865, 763, 657.

Example 8

Catalyst Fe3

According to general preparation procedure D, 0.71 g of iron (III) tris(acetylacetonate) and 7.26 g of 1,3-ketoamide 6 were reacted. One obtained 7.69 g of a brownish red oil.

FT-IR: 2967, 2865, 1638, 1558, 1512, 1456, 1372, 1335, 1296, 1095, 1013, 926, 865, 763, 657.

Example 9

Catalyst Fe4

According to general preparation procedure D, 3.54 g of iron (III) tris(acetylacetonate), 3.99 g of N,N-dibutyl-3-oxoheptane amide and 5.32 g of 1,3-Ketoamid 3 were reacted. One obtained 10.32 g of a dark red oil.

FT-IR: 2957, 2930, 2871, 1636, 1556, 1511, 1461, 1370, 1331, 1271, 1226, 1200, 1102, 1019, 986, 956, 763, 661.

General Preparation Procedure E

In a round-bottom flask, zinc (II) bis(acetylacetonate) hydrate (contains around 2 equivalents of water) and a 1,3-ketoamide prepared as described were mixed and the mixture heated under stirring for 3 hours to 90° C. After this, the reaction mixture was liberated of volatile components in vacuum.

Example 10

Catalyst Zn1

According to general preparation procedure E, 2.53 g of zinc (II) bis(acetylacetonate) hydrate and 17.99 g of 1,3-ketoamide 7 were reacted. One obtained 18.24 g of a light yellow oil.

FT-IR: 3325, 2968, 2867, 1652, 1547, 1450, 1372, 1341, 1298, 1263, 1096, 1015, 964, 925, 866, 782.

Example 11

Catalyst Zn2

According to general preparation procedure E, 1.33 g of zinc (II) bis(acetylacetonate) hydrate and 15.57 g of 1,3-ketoamide 2 were reacted. One obtained 16.15 g of a light yellow oil.

FT-IR: 2969, 2930, 2866, 1718, 1637, 1587, 1517, 1450, 1372, 1341, 1296, 1259, 1094, 1014, 925, 866, 768.

Example 12

Catalyst Zn3

According to general preparation procedure E, 1.31 g of zinc (II) bis(acetylacetonate) hydrate and 9.04 g of 1,3-ketoamide 3 were reacted. One obtained 9.49 g of a light yellow oil.

FT-IR: 2968, 2927, 2874, 1717, 1634, 1579, 1513, 1444, 1372, 1333, 1258, 1199, 1100, 1017, 927, 859, 769.

Example 13

Catalyst Zn4

According to general preparation procedure E, 0.86 g of zinc (II) bis(acetylacetonate) hydrate and 9.77 g of 1,3-ketoamide 8 were reacted. One obtained 9.88 g of a light brown oil.

FT-IR: 3325, 2865, 1712, 1666, 1585, 1546, 1451, 1348, 1251, 1095, 995, 947, 849, 780.

General Preparation Procedure F

In a round-bottom flask, Coscat® 83 (bismuth (III) tris (neodecanoate) in neodecanoic acid; 16% Bi; from Erbslöh) and a 1,3-ketoamide prepared as described were mixed and the mixture was heated under stirring for 2 hours to 80° C. After this, the reaction mixture was cooled to room temperature.

Example 14

Catalyst Bi1

According to general preparation procedure F, 1.51 g of Coscat® 83 and 3.98 g of 1,3-ketoamide 2 were reacted. One obtained 5.48 g of a light yellow oil.

FT-IR: 2967, 2929, 2867, 1721, 1636, 1609, 1539, 1458, 1372, 1342, 1296, 1253, 1097, 1013, 926, 867.

Example 15

Catalyst Bi2

According to general preparation procedure F, 2.76 g of Coscat® 83 and 1.40 g of 1,3-ketoamide 4 were reacted. One obtained 4.16 g of a light yellow oil.

FT-IR: 3330, 2959, 2931, 2874, 1698, 1636, 1544, 1460, 1360, 1254, 1156, 1108, 1015, 908, 817, 741.

Example 16

Catalyst Bi3

According to general preparation procedure F, 1.38 g of Coscat® 83 and 2.18 g of 1,3-ketoamide 3 were reacted. One obtained 3.56 g of a light yellow oil.

FT-IR: 2964, 2932, 2873, 1717, 1635, 1602, 1459, 1372, 1341, 1102, 1021, 928, 817, 772.

Example 17

Catalyst Bi4

According to general preparation procedure F, 1.45 g of Coscat® 83 and 1.39 g of 1,3-ketoamide 4 were reacted. One obtained 2.84 g of a light yellow oil.

FT-IR: 3304, 2962, 2932, 2872, 1714, 1644, 1545, 1458, 1359, 1253, 1153, 1106, 1022, 923, 817, 741.

General Preparation Procedure G

In a round-bottom flask, zirconium (IV) propoxide solution (70% in propanol; 19.5% Zr) and a 1,3-ketoamide prepared as described were mixed and stirred for 3 hours at room temperature. After this, the reaction mixture was heated to 60° C. and partly liberated of volatile components in vacuum.

Example 36

Catalyst Zr1

According to general preparation procedure G, 1.28 g of zirconium (IV) propoxide solution and 13.54 g of 1,3-ketoamide 3 were reacted. One obtained 14.70 g of a viscous, light yellow oil.

FT-IR: 2970, 2931, 2871, 1717, 1635, 1568, 1516, 1445, 1372, 1333, 1257, 1202, 1100, 1018, 989, 963, 928, 861, 764, 740, 721, 668.

Example 37

Catalyst Zr2

According to general preparation procedure G, 2.05 g of zirconium (IV) propoxide solution and 30.66 g of 1,3-ketoamide 2 were reacted. One obtained 31.27 g of a viscous, orange-colored oil.

FT-IR: 2970, 2930, 2867, 1718, 1640, 1568, 1517, 1455, 1372, 1339, 1297, 1267, 1100, 1013, 990, 864, 925, 866, 834, 764, 668.

Example 38

Catalyst Zr3

According to general preparation procedure G, 1.42 g of zirconium (IV) propoxide solution and 9.86 g of 1,3-ketoamide 9 were reacted. One obtained 10.04 of a viscous, light yellow oil.

Two-Component Polyurethane Compositions

Examples 18 to 21 and 39 and Comparison Examples V1 to V5

For the preparation of the first component, for each example a polyether triol (Voranol® CP 4755, from Dow) and a catalyst according to Table 1 were intimately mixed in a centrifugal mixer (SpeedMixer™ DAC 150, FlackTek Inc.) for 30 seconds at 3000 rpm. A portion of the freshly prepared first component was then placed in an interior-lacquered aluminum tube, this was closed air-tight and kept for 7 days in a circulating air oven at 60° C.

The remaining potion of the freshly prepared first component was mixed in the manner described for each example with a modified diphenylmethane diisocyanate (Desmodur® CD-L, from Bayer), liquid at room temperature, as the second component according to Table 1 to form a polyurethane composition.

Likewise, for each example, the first component that was kept for 7 days at 60° C. was mixed with the second component according to Table 1 in the same manner to form a polyurethane composition.

The polyurethane compositions were tested for appearance, time until tack-free, bubble formation, Shore A hardness, and this both for the composition with the freshly prepared first component and for the composition with the first component kept for 7 days at 60° C. Furthermore, only for the composition with the freshly prepared first component the mechanical properties were measured in the tensile strength test, and this before and after various storage times for accelerated aging of the samples.

The appearance of the composition was judged purely visually and given a grade of "clear", "cloudy" or inhomogeneous ("inh.").

To determine the time until tack-free (skin formation time), the compositions at room temperature were applied in a layer thickness of around 3 mm to cardboard and the time was determined in normal climate ("NK"; 23±1° C., 50±5% relative humidity) until when the surface of a composition was touched lightly by means of a pipette of LDPE there was no longer any residue on the pipette for the first time.

The bubble formation was judged visually by means of the quantity ("many", "some", "none") of gas bubbles occurring during the hardening for the composition used to determine the skin formation time.

The Shore A hardness was determined by DIN 53505 on test bodies cured for 7 days in normal climate.

To determine the mechanical properties in the tensile strength test, films of around 3 mm thickness were prepared from the compositions, by pouring out the composition into a flat PTFE mold and curing for 7 days in the normal climate. Tack-free and elastic films were obtained. From the films, dumbbells were punched out with a length of 75 mm, web length of 30 mm and web width of 4 mm and one part of these was tested according to DIN EN 53504 at a pulling rate of 200 mm/min for tensile strength, elongation at break, and E modulus (at 0.5 to 5.0% elongation). The remaining part of the dumbbells was kept for 1 day at 100° C. in the circulating air oven and for 10 days under "Kataplasma" (40° C. and 100% relative humidity), or for 10 days under "Kataplasma" and 1 day at 100° C., then each was kept for one day in the normal climate and tested as described according to DIN EN 53504.

The results of these tests are given in Table 2.

It is evident from Table 2 that the two-component polyurethane compositions with the catalysts according to the invention constitute clear, homogeneous mixtures, which have relatively short skin formation times both before and after storage and harden bubble-free into a material with relatively high strength and good toughness.

TABLE 1

Two-component polyurethane compositions (quantities in parts by weight).

| Example | 18 | V1 | 19 | V2 | 20 | V3 | 21 | V4 | 39 | V5 |
|---|---|---|---|---|---|---|---|---|---|---|
| *First component:* | | | | | | | | | | |
| Voranol ® CP 4755 | 50 | 50 | 50 | 50 | 50 | 50 | 50 | 50 | 50 | 50 |
| Catalyst Mo5 | 0.34 | — | — | — | — | — | — | — | — | — |
| MoO$_2$(acac)$_2$[a] | — | 0.30 | — | — | — | — | — | — | — | — |
| Catalyst Fe1 | — | — | 0.58 | — | — | — | — | — | — | — |
| Fe(acac)$_3$[b] | — | — | — | 0.43 | — | — | — | — | — | — |
| Catalyst Zn3 | — | — | — | — | 0.27 | — | — | — | — | — |
| Zn(acac)$_2$[c] | — | — | — | — | — | 0.20 | — | — | — | — |
| Catalyst Bi4 | — | — | — | — | — | — | 0.026 | — | — | — |
| Coscat ® 83[d] | — | — | — | — | — | — | — | 0.013 | — | — |
| Catalyst Zr1 | — | — | — | — | — | — | — | — | 1.08 | — |
| Bicat ® 4130[f] | — | — | — | — | — | — | — | — | — | 0.15 |
| mmoi-equiv./100 g[e] | 0.37 | 0.41 | 0.45 | 0.45 | 0.23 | 0.23 | 0.018 | 0.018 | 0.36 | 0.36 |
| *Second component:* | | | | | | | | | | |
| Desmodur ® CD-L | 5.10 | 5.10 | 5.10 | 5.10 | 5.10 | 5.10 | 5.10 | 5.10 | 5.10 | 5.10 |

[a] 25% suspension of dioxomolybdän (VI) bis(acetylacetonate) in N-ethyl-2-pyrrolidone.
[b] 20.6% suspension of iron (III) tris(acetylacetonate) in N-ethyl-2-pyrrolidone.
[c] 19.3% suspension of zinc (II) bis(acetylacetonate) hydrate in methylethylketone.
[d] Bismuth tris(neodecanoate) in neodecanoic acid (16% Bi, from Erbslöh).
[f] Zirconium tetrakis(neodecanoate) (12.1% Zr, from Shepherd).
[e] mmol-equivalents of metal atoms of the catalyst per 100 g of composition.

TABLE 2

Properties of the two-component polyurethane compositions

| Example | 18 | V1 | 19 | V2 | 20 | V3 | 21 | V4 | 39 | V5 |
|---|---|---|---|---|---|---|---|---|---|---|
| *Composition with freshly prepared first component:* | | | | | | | | | | |
| Appearance | clear | inh. | clear | inh. | clear | inh. | clear | clear | clear | clear |
| Skin forming time (min.) | 20 | 18 | 35 | 120 | 83 | 85 | 25 | 160 | 35 | 300 |
| Shore A hardness | 43 | 42 | 44 | 32 | 40 | 45 | 47 | 44 | 46 | <20 |
| Bubble formation | none | none | none | some | none | none | none | none | none | some |
| Tensile strength (MPa): 7d/NK | 0.90 | 0.84 | 0.90 | 0.78 | 0.82 | 1.00 | 0.90 | 1.08 | 0.85 | 0.34 |
| + 10d/Kataplasma | 0.97 | 0.90 | 0.96 | 0.75 | 0.77 | 0.74 | 0.77 | 0.76 | 0.94 | 0.34 |
| + 1d/100° C. | 0.91 | 0.89 | 0.82 | 0.93 | 0.86 | 0.90 | 0.84 | 0.94 | 0.82 | 0.38 |
| + 10d/Kataplasma + 1d/100° C. | 1.00 | 0.85 | 0.97 | 0.73 | 0.97 | 0.98 | 0.89 | 0.85 | 0.82 | 0.35 |
| Elongation at break (%): 7d/N | 70 | 62 | 63 | 86 | 119 | 94 | 87 | 129 | 81 | 54 |
| + 10d/Kataplasma | 82 | 72 | 70 | 89 | 107 | 62 | 74 | 74 | 100 | 61 |
| + 1d/100° C. | 85 | 71 | 181 | 97 | 85 | 64 | 96 | 99 | 113 | 104 |
| + 10d/Kataplasma + 1d/100° C. | 95 | 62 | 81 | 83 | 114 | 74 | 97 | 87 | 92 | 86 |
| E modulus (MPa): 7d/NK | 1.99 | 1.91 | 1.92 | 1.46 | 1.00 | 1.75 | 1.60 | 1.39 | 1.46 | 0.81 |
| + 10d/Kataplasma | 1.75 | 2.16 | 1.96 | 1.30 | 1.25 | 1.63 | 1.62 | 1.48 | 1.54 | 0.62 |
| + 1d/100° C. | 1.68 | 1.95 | 0.65 | 1.28 | 1.58 | 1.96 | 1.42 | 1.55 | 1.26 | 0.54 |
| + 10d/Kataplasma + 1d/100° C. | 1.70 | 1.94 | 1.65 | 1.34 | 1.42 | 1.89 | 1.52 | 1.47 | 1.39 | 0.59 |
| *Composition with first component from storage:* | | | | | | | | | | |
| Appearance | clear | clear | clear | inh. | clear | clear | clear | clear | clear | clear |
| Skin forming time (min.) | 15 | 7 | 34 | 73 | 80 | 70 | 50 | >300 | 24 | >300 |
| Shore A hardness | 48 | 41 | 46 | 37 | 45 | 45 | 48 | 45 | 46 | <20 |
| Bubble formation | none | none | none | none | none | some | none | some | none | some |

Examples 22 to 41

As described for Example 18, each time for the preparation of the first component a polyether triol (Voranol® CP 4755, from Dow) and a catalyst according to Table 3 were mixed. A portion of the freshly prepared first component was then placed in an interior-lacquered aluminum tube, this was closed air-tight and kept for 7 days in a circulating air oven at 60° C.

The remaining potion of the freshly prepared first component was mixed in the manner described for example 18 with a modified diphenylmethane diisocyanate (Desmodur® CD-L, from Bayer), liquid at room temperature, as the second component according to Table 3 to form a polyurethane composition.

Likewise, for each example, the first component that was kept for 7 days at 60° C. was mixed with the second component according to Table 3 in the same manner to form a polyurethane composition.

The polyurethane compositions were tested as in Example 18 for appearance, time until tack-free, bubble formation, Shore A hardness, as well as mechanical properties in the tensile strength test.

The results of these tests are given in Table 4.

It is evident from Table 4 that the two-component polyurethane compositions with the catalysts according to the invention constitute clear, homogeneous mixtures, which have relatively short skin formation times both before and after storage and harden largely bubble-free into a material with good Shore A hardness.

TABLE 3

Two-component polyurethane compositions.

| Example | 22 | 23 | 24 | 25 | 26 | 27 | 28 | 29 | 30 | 31 | 32 | 33 | 34 | 35 | 40 | 41 |
|---|---|---|---|---|---|---|---|---|---|---|---|---|---|---|---|---|
| First component: | | | | | | | | | | | | | | | | |
| Voranol ® CP 4755 | 30 | 30 | 30 | 30 | 30 | 30 | 30 | 30 | 30 | 30 | 30 | 30 | 30 | 30 | 30 | 30 |
| Catalyst Mo1 | 0.31 | — | — | — | — | — | — | — | — | — | — | — | — | — | — | — |
| Catalyst Mo2 | — | 0.26 | — | — | — | — | — | — | — | — | — | — | — | — | — | — |
| Catalyst Mo3 | — | — | 0.31 | — | — | — | — | — | — | — | — | — | — | — | — | — |
| Catalyst Mo4 | — | — | — | 0.97 | — | — | — | — | — | — | — | — | — | — | — | — |
| Catalyst Mo5 | — | — | — | — | 0.67 | — | — | — | — | — | — | — | — | — | — | — |
| Catalyst Fe2 | — | — | — | — | — | 1.43 | — | — | — | — | — | — | — | — | — | — |
| Catalyst Fe3 | — | — | — | — | — | — | 1.16 | — | — | — | — | — | — | — | — | — |
| Catalyst Fe4 | — | — | — | — | — | — | — | 0.36 | — | — | — | — | — | — | — | — |
| Catalyst Zn1 | — | — | — | — | — | — | — | — | 0.43 | — | — | — | — | — | — | — |
| Catalyst Zn2 | — | — | — | — | — | — | — | — | — | 0.73 | — | — | — | — | — | — |
| Catalyst Zn4 | — | — | — | — | — | — | — | — | — | — | 0.66 | — | — | — | — | — |
| Catalyst Bi1 | — | — | — | — | — | — | — | — | — | — | — | 0.038 | — | — | — | — |
| Catalyst Bi2 | — | — | — | — | — | — | — | — | — | — | — | — | 0.016 | — | — | — |
| Catalyst Bi3 | — | — | — | — | — | — | — | — | — | — | — | — | — | 0.049 | — | — |
| Catalyst Zr2 | — | — | — | — | — | — | — | — | — | — | — | — | — | — | 1.25 | — |
| Catalyst Zr3 | — | — | — | — | — | — | — | — | — | — | — | — | — | — | — | 0.60 |
| mmol-equiv./100 g[a] | 1.17 | 1.19 | 1.15 | 1.17 | 1.19 | 1.02 | 0.89 | 1.04 | 0.59 | 0.59 | 0.57 | 0.024 | 0.025 | 0.044 | 0.32 | 0.33 |
| Second component: | | | | | | | | | | | | | | | | |
| Desmodur ® CD-L | 3.10 | 3.10 | 3.10 | 3.10 | 3.10 | 3.10 | 3.10 | 3.10 | 3.10 | 3.10 | 3.10 | 3.10 | 3.10 | 3.10 | 3.10 | 3.10 |

[a]mmol-equivalents of metal atoms of catalyst per 100 g of composition.

TABLE 4

Properties of the two-component polyurethane compositions.

| Example | 22 | 23 | 24 | 25 | 26 | 27 | 28 | 29 | 30 | 31 | 32 | 33 | 34 | 35 | 40 | 41 |
|---|---|---|---|---|---|---|---|---|---|---|---|---|---|---|---|---|
| Composition with freshly prepared first component: | | | | | | | | | | | | | | | | |
| Appearance | clear | clear | clear | clear | clear | clear | clear | clear | clear | clear | clear | clear | clear | clear | clear | clear |
| Skin forming time (min.) | 50 | 15 | 20 | 8 | 9 | 60 | 44 | 32 | 7 | 10 | 7 | 2 | 1 | 4 | 10 | 20 |
| Shore A hardness | 44 | 46 | 45 | 39 | 43 | 41 | 45 | 46 | 41 | 43 | 49 | 47 | 49 | 50 | 47 | 48 |
| Bubble formation | none | none | none | none | none | none | none | none | none | none | none | none | none | none | none | none |
| Composition with first component from storage: | | | | | | | | | | | | | | | | |
| Appearance | clear | clear | clear | clear | clear | clear | clear | clear | clear | clear | clear | clear | clear | clear | clear | clear |
| Skin forming time (min.) | 40 | 14 | 9 | 15 | 4 | 55 | 40 | 37 | 9 | 9 | 5 | 5 | 4 | 9 | 18 | 30 |
| Shore A hardness | 45 | 45 | 47 | 47 | 47 | 47 | 46 | 48 | 48 | 46 | 45 | 48 | 47 | 48 | 47 | 48 |
| Bubble formation | none | none | none | none | none | none | none | none | none | none | none | none | none | none | none | none |

The invention claimed is:

1. A metal complex compound of formula $M_k(L)_x(Y)_{kz-nx}$, where:
   M stands for a z-valent metal cation chosen from metal cations and oxometal cations of transitional metals, zinc, or main metal group elements of periodic table groups 13 to 15,
   k stands for a whole number in a range of from 1 to 20,
   x stands for 1, 2, 3 or 4,
   z stands for 2, 3 or 4,
   n stands for 2 or 3,
   Y stands for a single negatively charged ligand,
   L stands for a ligand of formula (I), and
   kz-nx may be 0, where:
   each of $R^1$ and $R^2$ independently stands for a hydrogen residue, a monovalent saturated or unsaturated hydrocarbon residue with 1 to 10 carbon atoms, or together stand for a divalent alkylene residue with 3 to 6 carbon atoms,
   $R^3$ stands for a hydrogen residue or a monovalent saturated hydrocarbon residue with 1 to 12 carbon atoms that optionally contains heteroatoms, and
   A stands for a polyoxyalkylene-containing residue with a mean molecular weight $M_n$ of 200 to 5000 g/mol, optionally with one or two terminal 1,3-ketoamide groups of formula

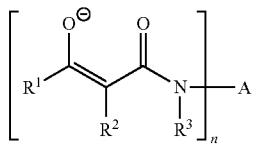

(I)

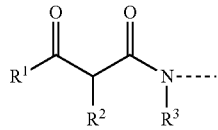

2. The metal complex compound according to claim 1, wherein the metal cation is a metal cation or oxometal cation of scandium, yttrium, lanthanum, titanium, zirconium, hafnium, vanadium, niobium, tantalum, chromium, molybdenum, tungsten, manganese, iron, cobalt, nickel, copper, zinc, aluminum, gallium, indium, germanium, tin, lead, antimony, or bismuth.

3. The metal complex compound according to claim 1, wherein the metal cation or oxometal cation is a dioxomolybdenum (VI), iron (III), zinc (II), bismuth (III), or zirconium (IV) cation.

4. The metal complex compound according to claim 1, wherein $R^1$ stands for an alkyl residue with 1 to 4 carbon atoms.

5. The metal complex compound according to claim 1, wherein $R^2$ stands for a hydrogen residue.

6. The metal complex compound according to claim 1, wherein $R^3$ stands for a hydrogen residue or an alkyl residue with 1 to 8 carbon atoms.

7. The metal complex compound according to claim 1, wherein n is 2.

8. A method for producing the metal complex compound according to claim 1, comprising reacting a 1,3-ketoamide with a metal salt or metal complex chosen from a salt or a complex of a transitional metal, zinc, or an element of main metal group elements of periodic table groups 13 to 15, wherein the 1,3-ketoamide has a formula:

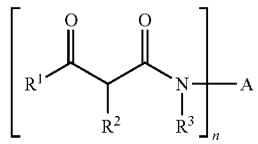

where:
each of $R^1$ and $R^2$ independently stands for a hydrogen residue, a monovalent saturated or unsaturated hydrocarbon residue with 1 to 10 carbon atoms, or together stand for a divalent alkylene residue with 3 to 6 carbon atoms,
$R^3$ stands for a hydrogen residue or a monovalent saturated hydrocarbon residue with 1 to 12 carbon atoms that optionally contains heteroatoms, and
A stands for a polyoxyalkylene-containing residue, optionally with one or two terminal 1,3-ketoamide groups of formula

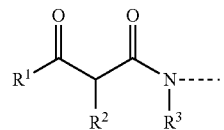

9. The method according to claim 8, wherein the metal salt or metal complex are chlorides, carbonates, carboxylates, or 1,3 diketonates.

10. The metal complex compound according to claim 1, wherein the polyoxyalkylene-containing residue is a polyoxypropylene amine, which optionally contains moieties of oxybutylene and/or oxyethylene units.

11. A metal complex compound, obtained by reacting a 1,3-ketoamide with a metal salt or a metal complex chosen from a salt or a complex of a transitional metal, zinc, or an element of main metal group elements of periodic table groups 13 to 15;
wherein the 1,3-ketoamide has a formula:

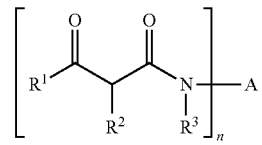

where:
each of $R^1$ and $R^2$ independently stands for a hydrogen residue, a monovalent saturated or unsaturated hydrocarbon residue with 1 to 10 carbon atoms, or together stand for a divalent alkylene residue with 3 to 6 carbon atoms,
$R^3$ stands for a hydrogen residue or a monovalent saturated hydrocarbon residue with 1 to 12 carbon atoms that optionally contains heteroatoms,
A stands for a polyoxyalkylene-containing residue with a mean molecular weight $M_n$ of 200 to 5000 g/mol, optionally with one or two terminal 1,3-ketoamide groups of formula

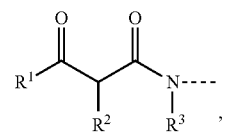

and
n stands for 2 or 3.

12. A metal complex compound of formula $M_k(L)_x(Y)_{kz-nx}$, where:
M stands for a z-valent metal cation chosen from metal cations and oxometal cations of scandium, yttrium, lanthanum, titanium, zirconium, hafnium, vanadium, niobium, tantalum, chromium, molybdenum, tungsten, manganese, cobalt, nickel, copper, zinc, aluminum, gallium, indium, germainium, tin, lead, antimony, or bismuth,
k stands for a whole number in a range of from 1 to 20,
x stands for 1, 2, 3 or 4,
z stands for 2, 3, or 4,
n stands for 1, 2, or 3,
Y stands for a single negatively charged ligand,
L stands for a ligand of formula (I), and
kz-nx may be 0,

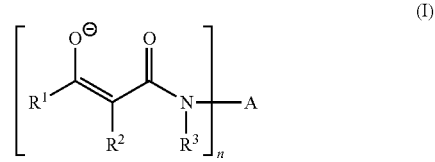

where:
each of $R^1$ and $R^2$ independently stands for a hydrogen residue, a monovalent saturated or unsaturated hydrocarbon residue with 1 to 10 carbon atoms, or together stand for a divalent alkylene residue with 3 to 6 carbon atoms, $R^3$ stands for a hydrogen residue or a monovalent saturated hydrocarbon residue with 1 to 12 carbon atoms that optionally contains heteroatoms, and A stands for a polyoxyalkylene-containing residue with a mean molecular weight $M_n$ of 200 to 5000 g/mol, optionally with one or two terminal 1,3-ketoamide groups of formula

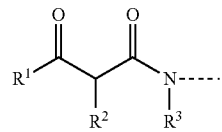

13. A method comprising:
mixing the metal complex compound according to claim 1 with a curable mass to catalyze curing of the curable mass.

14. A two-component polyurethane composition, comprising at least one polyol as a first component, at least one polyisocyanate as a second component, and at least one metal complex compound according to claim 1.

15. The two-component polyurethane composition according to claim 13, wherein the metal complex compound is contained in the first component.

16. A casting compound, sealant, adhesive, lining, coating, lacquer, primer, molded piece, or elastomer for construction and industrial applications comprising:
the two-component polyurethane composition according to claim 13.

* * * * *